United States Patent
Mita et al.

(10) Patent No.: US 12,360,117 B2
(45) Date of Patent: Jul. 15, 2025

(54) METHOD FOR DETERMINING GLOMERULAR FILTRATION ABILITY

(71) Applicants: Kagami Inc., Ibaraki (JP); National Institutes of Biomedical, Innovation, Health and Nutrition, Ibaraki (JP)

(72) Inventors: Masashi Mita, Tokyo (JP); Tatsuhiko Ikeda, Tokyo (JP); Tomonori Kimura, Tokyo (JP)

(73) Assignees: Kagami Inc., Osaka (JP); National Institutes of Biomedical Innovation, Health and Nutrition, Osaka (JP)

( * ) Notice: Subject to any disclaimer, the term of this patent is extended or adjusted under 35 U.S.C. 154(b) by 1007 days.

(21) Appl. No.: 17/286,359

(22) PCT Filed: Oct. 17, 2019

(86) PCT No.: PCT/JP2019/040960
§ 371 (c)(1),
(2) Date: Apr. 16, 2021

(87) PCT Pub. No.: WO2020/080484
PCT Pub. Date: Apr. 23, 2020

(65) Prior Publication Data
US 2021/0373031 A1    Dec. 2, 2021

(30) Foreign Application Priority Data

Oct. 17, 2018 (JP) .................. 2018-196251

(51) Int. Cl.
*G01N 33/68* (2006.01)
*A61P 13/12* (2006.01)

(52) U.S. Cl.
CPC .......... *G01N 33/6812* (2013.01); *A61P 13/12* (2018.01); *G01N 2400/10* (2013.01); *G01N 2800/347* (2013.01)

(58) Field of Classification Search
CPC ......... G01N 33/6812; G01N 2800/347; G01N 2400/10; A61P 13/12
See application file for complete search history.

(56) References Cited

U.S. PATENT DOCUMENTS

2015/0079623 A1    3/2015    Hamase et al.

FOREIGN PATENT DOCUMENTS

WO    WO-2013/140785 A1    9/2013
WO    WO2017200024 A1 *    11/2017

OTHER PUBLICATIONS

Chouhan et al. A Brief Review of Diagnostic Techniques and Clinical Management in Chronic Kidney Disease. Cureus 15(11): e49030, 2023.*
English language translation of WO2017200024-A1; Nov. 23, 2017.*
Gaitonde et al. Chronic Kidney Disease: Detection and Evaluation. Am Fam Physicia 96(12): 776-783, 2017.*
Kimura et al. Supplemental Information from article: Chiral amino acid metabolomics for novel biomarker screening in the prognosis of chronic kidney disease. Sci Reports 6: 26137, 2016.*
Fukushima et al., "Determination of D-Amino Acids in Serum from Patients with Renal Dysfunction," Biol. Pharm. Bull., 1995, 18(8):1130-1132.
Huang et al., "Urinary Excretion of D-Serine in Human: Comparison of Different Ages and Species," Biol. Pharm. Bull, 1998, 21(2):156-162.
Ishida, Hironori, "Serum D-Amino Acid Elucidated in Renal Failure," Kitasato Medical Journal, 1993, 23:51-62, with English abstract.
Kimura et al., "Chiral amino acid metabolomics for novel biomarker screening in the prognosis of chronic kidney disease," Scientific Reports, May 18, 2016, 6(26137):1-7.
Nagata et al., "Neutral free D-amino acids present in human plasma," Viva Origino, Jul. 1990, 18(2), 15th Lecture Meeting Abstracts, with partial English translation.
Hesaka et al., "D-Serine reflects kidney function and diseases," Scientific Reports, Mar. 25, 2019, 9(1):5104, 1-8.
Sasabe et al., "Ischemic Acute Kidney Injury Perturbs Homeostasis of Serine Enantiomers in the body fluid in Mice: Early Detection of Renal Dysfunction Using the Ratio of Serine Enantiomers," PLOS ONE, Jan. 2014, 9(1): e86507, 1-9.

* cited by examiner

Primary Examiner — Bridget E Bunner
(74) Attorney, Agent, or Firm — Foley & Lardner LLP

(57) ABSTRACT

The present invention provides a method for determining glomerular filtration ability on the basis of the amount of D-serine in the blood. The present invention provides a blood analysis system which includes a storage unit, an analysis measurement unit, a data processing unit and a glomerular filtration ability output unit, wherein: the storage unit stores the correlation equation between the amount of D-serine in the blood and glomerular filtration ability; the analysis measurement unit separates and quantifies the amount of D-serine in the blood; the data processing unit calculates glomerular filtration ability by inputting the D-serine amount into the correlation equation stored in the storage unit; and a pathology information output unit outputs glomerular filtration ability information.

2 Claims, 5 Drawing Sheets

METHOD FOR DETERMINING GLOMERULAR FILTRATION ABILITY

CROSS-REFERENCE TO RELATED APPLICATIONS

This application is the U.S. National Stage of PCT/JP2019/040960, filed Oct. 17, 2019, which claims priority to JP 2018-196251, filed Oct. 17, 2018.

FIELD

The present invention relates to a method of determining glomerular filtration capacity and to a blood analysis system that determines glomerular filtration capacity.

BACKGROUND

Glomerular filtration rate (GFR) is a typical marker for indication of renal function. The glomerular filtration rate represents the liquid volume filtered per minute from blood by the glomeruli, with inulin clearance considered to be the international gold standard. However, measurement of inulin clearance requires continuous drip infusion of inulin over a period of 2 hours as well as urine and blood collection multiple times, which creates a burden for both the patient and the practitioner. For routine practice in the clinic, therefore, measurement of inulin clearance is only carried out for limited situations such as donors for live kidney transplant, while for most cases it is substituted by measurement of other markers such as creatinine. Most marker values, however, diverge significantly from the actual glomerular filtration rate according to the gold standard of inulin clearance, thus interfering with accurate diagnosis of kidney disease.

Creatinine is routinely measured in the clinic as a marker for renal function. Creatinine is the final metabolite of creatine which is necessary for muscle contraction. Creatine formed in the liver is taken up into muscle cells and partially metabolized to creatinine, transported to the kidneys through the blood, filtered by the glomeruli, and then excreted into urine in the renal tubules without being reabsorbed. It is utilized for evaluation of renal function because it can serve as an advantageous marker for uremia, since reduced glomerular filtration capacity leads to impaired discharge and accumulation in the blood causing its numerical value to increase. However, the amount of creatinine in blood does not appear as a clearly abnormal value until GFR has reduced by 50% or greater, and it therefore cannot be considered to be a sensitive marker.

Cystatin C is a protein of 13.36 kDa molecular weight that is produced in a fixed proportion by systemic nucleated cells, and is completely filtered out by the glomeruli and subsequently decomposed in the kidneys via reabsorption in the renal tubules, and since it is therefore thought to be removed from the blood depending on the filtration rate, its amount in blood serves as a GFR marker. When renal function is greatly reduced, however, the amount of increase in blood cystatin C reaches a plateau, and in end-stage kidney disease it becomes difficult to accurately evaluate renal function.

Thus, no biomarker has yet existed that can adequately meet clinical demands for accurately measuring glomerular filtration rate for individual patients in a wide range from early to late stage by blood collection alone, without a large burden on subjects or patients.

Conventionally, D-amino acids had been considered to be absent from the body of mammals, but they have since been shown to be present in various tissues and to carry out physiological functions. It has been shown that the amounts of D-serine, D-alanine, D-proline, D-glutamic acid and D-aspartic acid in blood can serve as kidney failure markers since they vary in kidney failure patients and correlate with creatinine (NPL 1, NPL 2, NPL 3, NPL 4). It has also been disclosed that amino acids selected from the group consisting of D-serine, D-threonine, D-alanine, D-asparagine, D-allothreonine, D-glutamine, D-proline and D-phenylalanine serve as pathology marker values for kidney disease (PTL 1). The aforementioned publications merely disclose that the fluctuation of D-amino acids in the blood of patients suffering from kidney disease compared to healthy persons can be used as markers for diagnosis of kidney disease, or that D-serine blood levels of subjects correlate with creatinine levels or with estimated corrected creatinine levels, but nowhere suggest that D-amino acid blood levels directly correlate with the gold standard of inulin clearance and allow determination (estimation) of glomerular filtration capacity. Incidentally, while urine L-FABP, blood NGAL and urine KIM-1 have been disclosed as kidney disease markers in recent years, these do not correlate with glomerular filtration capacity.

CITATION LIST

Patent Literature

[PTL 1] International Patent Publication No. 2013/140785

Non Patent Literature

[NPL 1] Fukushima, T. et al., Biol. Pharm. Bull. 18: 1130 (1995)
[NPL 2] Nagata Y. Viva Origino Vol. 18(No. 2) (1990), 15th Lecture Meeting Abstracts
[NPL 3] Ishida et al., Kitasato Medical Journal 23:51-62 (1993)
[NPL 4] Yong Huang et al., Biol. Pharm. Bull. 21:(2)156-162 (1998)

SUMMARY

Technical Problem

There is a demand for a method of accurately determining glomerular filtration capacity in subjects across a wider range than with conventionally known renal function markers such as blood creatinine.

Solution to Problem

The present inventors, focusing on blood D-serine and analyzing its correlation with GFR (inulin clearance), found surprisingly that blood D-serine levels in blood samples from healthy persons and kidney disease patients in the early to late stages are more highly correlated with GFR (inulin clearance) than creatinine or cystatin C levels throughout all stages, and have completed this invention based on this finding.

The present invention thus relates to the following:
[1] A method of determining glomerular filtration capacity based on blood D-serine level.
[2] The method according to [1] above, wherein the glomerular filtration capacity is the glomerular filtration rate determined based on a formula calculated from the correlation between inulin clearance and blood D-serine level.

[3] The method according to [1] or [2] above, wherein the blood is blood of a subject assessed to have suspected kidney disease by an existing examination method.

[4] The method according to any one of [1] to [3] above, wherein treatment intervention is carried out for a subject assessed to have reduced glomerular filtration capacity.

[5] The method according to [4] above, wherein the treatment intervention is selected from the group consisting of lifestyle habit improvement, dietary guidance, blood pressure management, anemia management, electrolyte management, uremia management, blood sugar level management, immune management and lipid management.

[6] The method according to [4] or [5] above, wherein the treatment intervention includes administration to a subject of one or more drugs selected from the group consisting of diuretic drugs, calcium antagonists, angiotensin converting enzyme inhibitors, angiotensin receptor antagonists, sympatholytic drugs, SGLT2 inhibitors, sulfonylurea drugs, thiazolidine drugs, biguanide drugs, α-glucosidase inhibitors, glinide drugs, insulin formulations, NRF2 activators, immunosuppressive agents, statins, fibrates, anemia treatments, erythropoietin formulations, HIF-1 inhibitors, iron agents, electrolyte regulators, calcium receptor agonists, phosphorus adsorbents, uremic toxin adsorbents, DPP4 inhibitors, EPA formulations, nicotinic acid derivatives, cholesterol transporter inhibitors and PCSK9 inhibitors.

[7] A blood analysis system comprising a storage unit, an analytical measurement unit, a data processing unit and a glomerular filtration capacity output unit, wherein:
the storage unit stores a correlation formula between D-serine level and glomerular filtration capacity;
the analytical measurement unit separately quantifies the blood D-serine level;
the data processing unit applies the D-serine level to the correlation formula stored in the storage unit to calculate the glomerular filtration capacity; and
the pathological information output unit outputs information for the glomerular filtration capacity.

[8] The blood analysis system according to [7] above, wherein the glomerular filtration capacity is the glomerular filtration rate determined based on a formula calculated from the correlation between inulin clearance and blood D-serine level.

[9] The blood analysis system according to [7] or [8] above, wherein the blood is blood of a subject assessed to have suspected kidney disease by an existing examination method.

Advantageous Effects of Invention

The blood D-serine level to be used in the method of determining glomerular filtration capacity of the invention correlates better with GFR (inulin clearance) than blood creatinine or cystatin C levels.

DESCRIPTION OF EMBODIMENTS

Figure 1:
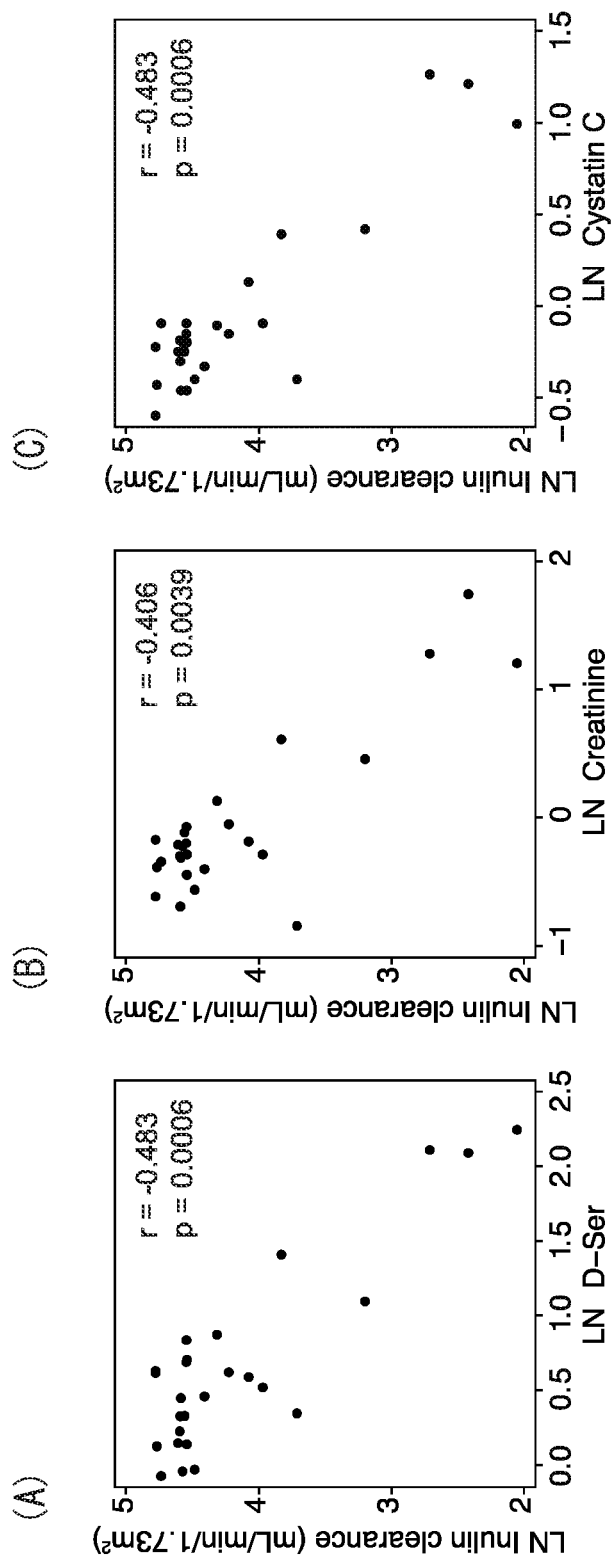
FIG. 1 is a set of scatter plots representing blood D-serine level (A), creatinine level (B) and cystatin C level (C) measured for subjects, with respect to GFR (inulin clearance) (corrected for body surface area).

The present invention relates to a method of determining glomerular filtration capacity based on blood D-serine level.

According to the invention, "glomerular filtration capacity" refers to the ability of the glomeruli to filter blood. According to one aspect, it is represented as the glomerular filtration rate (GFR), but the glomerular filtration capacity is not limited to the actual glomerular filtration rate and may be determined in arbitrary units. As an example, the blood D-serine level may be represented as the glomerular filtration capacity either directly or after correction by an arbitrary value depending on the case. According to the invention, the glomerular filtration capacity may be the glomerular filtration capacity corrected for body surface area, or it may be the glomerular filtration capacity without correction for body surface area. Because glomerular filtration capacity requirement differs depending on physical size, correction for body surface area is often used for comparison, statistical processing or screening diagnosis.

The glomerular filtration rate is represented in units of "mL/min", indicating the liquid volume filtered per minute from blood by the glomeruli. Since the glomerular filtration rate requirement varies according to physical size, it is corrected to the glomerular filtration rate per standard body surface area of 1.73 m$^2$ for statistical processing, comparison and screening diagnosis, and units of "mL/min/1.73 m$^2$" are used. While it is common to use the body surface area-corrected value for comparison and screening diagnosis of renal function, the value without body surface area correction is used for individual renal function diagnosis and dosage determination of renal excretion drugs. The glomerular filtration rate is clinically determined from the clearance for inulin, sodium thiosulfate, creatinine, iotalamic acid or sinistrin. The present invention determines the glomerular filtration capacity based on the correlation between blood D-serine level and GFR (inulin clearance).

According to the invention, D-serine used as the marker is the enantiomer of L-serine, a constituent amino acid of proteins. D-serine level is strictly regulated in the tissues and blood by metabolic enzymes such as serine racemase and D-amino acid oxidase, but the blood D-serine level varies with renal impairment.

According to the invention, "blood D-serine level" may refer to the D-serine level in a specific blood volume, or it may be represented as the concentration. The blood D-serine level is measured as the amount in a sample of blood that has been treated by centrifugal separation, sedimentation separation or other pretreatment for analysis. Therefore, the blood D-serine level can be measured as the amount in a blood sample derived from sampled whole blood, serum or blood plasma. For analysis using HPLC, for example, the D-serine level in a predetermined amount of blood is represented in a chromatogram, and the peak heights, areas and shapes may be quantified by analysis based on standard sample comparison and calibration. Comparison of the D-serine concentration with a known sample allows measurement of the D-serine concentration in blood, and the D-serine concentration in the blood may be used as the blood D-serine level. With an enzyme method, the amino acid concentration can be calculated by quantitative analysis using a standard calibration curve.

The D-serine and L-serine levels may be measured by any method, such as chiral column chromatography, or measurement using an enzyme method, or quantitation by an immunological method using a monoclonal antibody that distinguishes between enantiomers of amino acids. Measurement of the D-serine and L-serine levels in a sample according to the invention may be carried out using any method well known to those skilled in the art. Examples include chromatographic and enzyme methods (Y. Nagata et al., Clinical Science, 73 (1987), 105. Analytical Biochemistry, 150 (1985), 238, A. D'Aniello et al., Comparative Biochemistry and Physiology Part B, 66 (1980), 319. Journal of Neurochemistry, 29 (1977), 1053, A. Bememan et al., Journal of Microbial & Biochemical Technology, 2 (2010), 139, W. G. Gutheil et al., Analytical Biochemistry, 287 (2000), 196, G. Molla et al., Methods in Molecular Biology, 794 (2012), 273, T. Ito et al., Analytical Biochemistry, 371 (2007), 167), antibody methods (T. Ohgusu et al., Analytical Biochemistry, 357 (2006), 15), gas chromatography (GC) (H. Hasegawa et al., Journal of Mass Spectrometry, 46 (2011), 502, M. C. Waldhier et al., Analytical and Bioanalytical Chemistry, 394 (2009), 695, A. Hashimoto, T. Nishikawa et al., FEBS Letters, 296 (1992), 33, H. Bruckner and A. Schieber, Biomedical Chromatography, 15 (2001), 166, M. Junge et al., Chirality, 19 (2007), 228, M. C. Waldhier et al., Journal of Chromatography A, 1218 (2011), 4537), capillary electrophoresis methods (CE) (H. Miao et al., Analytical Chemistry, 77 (2005), 7190, D. L. Kirschner et al., Analytical Chemistry, 79 (2007), 736, F. Kitagawa, K. Otsuka, Journal of Chromatography B, 879 (2011), 3078, G. Thorsen and J. Bergquist, Journal of Chromatography B, 745 (2000), 389), and high-performance liquid chromatography (HPLC) (N. Nimura and T. Kinoshita, Journal of Chromatography, 352 (1986), 169, A. Hashimoto et al., Journal of Chromatography, 582 (1992), 41, H. Bruckner et al., Journal of Chromatography A, 666 (1994), 259, N. Nimura et al., Analytical Biochemistry, 315 (2003), 262, C. Muller et al., Journal of Chromatography A, 1324 (2014), 109, S. Einarsson et al., Analytical Chemistry, 59 (1987), 1191, E. Okuma and H. Abe, Journal of Chromatography B, 660 (1994), 243, Y. Gogami et al., Journal of Chromatography B, 879 (2011), 3259, Y. Nagata et al., Journal of Chromatography, 575 (1992), 147, S. A. Fuchs et al., Clinical Chemistry, 54 (2008), 1443, D. Gordes et al., Amino Acids, 40 (2011), 553, D. Jin et al., Analytical Biochemistry, 269 (1999), 124, J. Z. Min et al., Journal of Chromatography B, 879 (2011), 3220, T. Sakamoto et al., Analytical and Bioanalytical Chemistry, 408 (2016), 517, W. F. Visser et al., Journal of Chromatography A, 1218 (2011), 7130, Y. Xing et al., Analytical and Bioanalytical Chemistry, 408 (2016), 141, K. Imai et al., Biomedical Chromatography, 9 (1995), 106, T. Fukushima et al., Biomedical Chromatography, 9 (1995), 10, R. J. Reischl et al., Journal of Chromatography A, 1218 (2011), 8379, R. J. Reischl and W. Lindner, Journal of Chromatography A, 1269 (2012), 262, S. Karakawa et al., Journal of Pharmaceutical and Biomedical Analysis, 115 (2015), 123).

The separative analysis system for enantiomers according to the invention may be a combination of multiple separative analysis methods. More specifically, the D-/L-amino acid level in a sample can be measured using an enantiomer analysis method comprising a step of passing a sample containing a component with enantiomers through a first column filler as the stationary phase, together with a first liquid as the mobile phase, to separate the components in the sample, a step of separately holding each of the components in the sample in a multi loop unit, a step of passing each of the components in the sample that are separately held in the multi loop unit through a flow channel in a second column filler having an optically active center, as the stationary phase, together with a second liquid as the mobile phase, to separate the enantiomers among each of the sample components, and a step of detecting the enantiomers in each of the sample components (Japanese Patent No. 4291628). In HPLC analysis, D- and L-amino acids are sometimes prederivatized with a fluorescent reagent such as o-phthalaldehyde (OPA) or 4-fluoro-7-nitro-2,1,3-benzooxadiazole (NBD-F), or diastereomerized using an agent such as N-tert-butyloxycarbonyl-L-cysteine (Boc-L-Cys) (Hamase, K. and Zaitsu, K., Bunseki Kagaku, Vol. 53, 677-690 (2004)). Alternatively, the D-amino acids may be measured by an immunological method using a monoclonal antibody that distinguishes enantiomers of amino acids, such as a monoclonal antibody that specifically binds to D-serine or L-serine. When the total of the D-form and L-form is to be used as the marker it is not necessary to separate the D-form and L-form, allowing the amino acids to be analyzed without separating the D-form and L-form. In such cases as well, separation and quantitation may be carried out using an enzyme method, antibody method, GC, CE or HPLC.

Since the blood creatinine level to be used for comparison with the invention is significantly affected by the amount of muscle from which it is derived, sports athletes, acromegaly patients and persons that have ingested large amounts of meat will exhibit higher values, while patients suffering from neuromuscular disease (such as muscular dystrophy), emaciation, prolonged bed rest, frailty, sarcopenia, locomotive syndrome or amputation, or persons that have restricted their protein intake, will exhibit lower values, and therefore accurate renal function cannot be reflected. Moreover, since blood creatinine levels have been found to have circadian variation of about 10%, with higher values in the morning, care must also be taken in that regard. Since blood cystatin C level increases sharply compared to blood creatinine level with moderate reduction in renal function, it is considered to be advantageous for discovering early impaired renal function. However, it is also known that levels are affected by the use of steroids and cyclosporins, and by patient conditions such as diabetes, hyperthyroidism, inflammation, hyperbilirubinemia and hypertriglyceridemia. For examination of kidney disease, therefore, it is necessary to make a comprehensive diagnosis in combination with other markers such as urea nitrogen (BUN) and urine proteins.

The accuracy of the glomerular filtration rate determined based on conventional renal function markers such as blood creatinine levels is low, and while accurate glomerular filtration rate measurement is possible based on the gold standard of inulin clearance, it involves complex methods and a burden on patients and health care professionals, and is therefore limited in its practicality. The method of determining glomerular filtration capacity according to the invention at least allows the glomerular filtration capacity to be more accurately determined than by blood creatinine levels, and even allows glomerular filtration capacity to be determined more accurately than by blood cystatin C levels. When analysis was made in correlation with inulin clearance in groups classified according to glomerular filtration rate, D-serine exhibited higher correlation coefficient r values and higher correlation with inulin clearance, than both blood cystatin C and creatinine levels across all the groups. Future experiments should be conducted to determine accuracy, but it has the potential to equal or surpass the performance obtained by the glomerular filtration rate determining method based on inulin clearance, which is the international standard for measurement. According to another aspect of the invention, therefore, it is possible to use blood D-serine level as a substitute marker for inulin clearance. A substitute marker is a marker whose relationship with a final evaluation can be scientifically proven. Being a substitute marker for inulin clearance, therefore, means that glomerular filtration rate can be determined based on D-serine levels instead of using a GFR determining method based on inulin clearance, as a result of having used blood D-serine levels to statistically demonstrate a relationship with evaluation based on inulin clearance.

While it is not our intention to be limited to any particular theory, D-serine has the advantage of not being affected by muscle mass and thus not requiring correction for physical size as is necessary for blood creatinine. According to one aspect of the invention, the method of determining glomerular filtration rate of the invention is characterized by not correcting for one or more physical size-related factors selected from the group consisting of gender, age and muscle mass.

Blood creatinine level ($p=0.0074$) and cystatin C level ($p=0.043$) were observed to correlate with body surface area (BSA), but D-serine level ($p=0.17$) did not correlate with BSA (Example 3). This indicates that creatinine and cystatin C are affected by physical size including muscle mass, and that accurate glomerular filtration capacity measurement requires correction for race, age, gender and body surface area. Glomerular filtration capacity assessed by D-serine level, on the other hand, can provide accurate values that are not affected by reduced muscle or by physical size as with the elderly. Body surface area can be determined by a known method, and the following formula may be used as an example.

$$BSA = \text{Body weight (kg)}^{0.425} \times \text{body height (cm)}^{0.725} \times 0.007184 \quad \text{[Mathematical Formula 1]}$$

According to one aspect of the invention, the glomerular filtration capacity can be determined by substituting a patient blood D-serine level into a formula derived from the correlation between inulin clearance and blood D-serine level, or a corresponding table or graph. The correlation between inulin clearance and D-serine level has been shown to be higher than the correlation between inulin clearance and blood creatinine level, and therefore glomerular filtration capacity determined by substituting a patient D-serine level into a formula, or a table or graph, derived from the correlation between inulin clearance and blood D-serine level is more accurate than the conventional glomerular filtration rate determined based on blood creatinine level.

Inulin clearance used for analysis of correlation may be body surface area-corrected inulin clearance, or the inulin clearance before correcting for body surface area. Glomerular filtration capacity before or after correction for body surface area may be selected according to the need. A corresponding table derived from the correlation between inulin clearance and blood D-serine level may list values for glomerular filtration capacity corresponding to D-serine level, or it may list severity categories for kidney disease corresponding to numerical ranges.

The severity categories for chronic kidney disease (CKD) are the 6 levels of G1, G2, G3a, G3b, G4 and G5, according to the numerical ranges for glomerular filtration rate. Specifically, the definitions are normal or high value for 90 mL/min/1.73 m$^2$ or greater (G1), normal or mildly low for 60 to 89 mL/min/1.73 m$^2$ (G2), mildly to moderately low for 45 to 59 mL/min/1.73 m$^2$ (G3a), moderately to severely low for 30 to 44 mL/min/1.73 m$^2$ (G3b), severely low for 15 to 29 mL/min/1.73 m$^2$ (G4) and end-stage kidney disease for less than 15 mL/min/1.73 m$^2$ (G5) (Japanese Society of Nephrology Guidelines).

Various formulas have been devised for blood creatinine level or cystatin C level which is observed to correlate with physical size, estimating the glomerular filtration rate by correcting for race, age and gender using large-scale patient data. The major estimation formulas for glomerular filtration rate are the Cockcroft-Gault formula, MDRD formula and CKD-EPI formula, and currently the estimation formula (eGFR) used for routine examination for Japanese is the following.

eGFRcreat $$\text{(male) mL/min/1.73 m}^2 = 194 \times Cr^{1.094} \times age^{-0.287}$$

$$\text{(female) mL/min/1.73 m}^2 = 194 \times Cr^{1.094} \times age^{-0.287} \times 0.739 \quad \text{[Mathematical Formula 2]}$$

However, the eGFR determined in this manner is a marker created for health examination screening or for convenient evaluation in epidemiologic research for comparison of numerous subjects, with the values being intended to be calculated with correction to average physical size, and therefore it is still recommended to use inulin clearance for accurate evaluation of renal function for individual patients including excessively lean elderly (Japanese Society of Nephrology Guidelines).

When glomerular filtration capacity is determined by the evaluation method of the invention it is possible to classify the severity of kidney disease on the basis of the results. As an example, classification may be according to the 6 severity levels of G1, G2, G3a, G3b, G4 and G5, as categories for chronic kidney disease patients. Treatment intervention is used for subjects classified in categories corresponding to G2 to G5. The treatment intervention is selected as appropriate for each category. The treatment intervention is guidance for one or a combination from among lifestyle habit improvement, dietary guidance, blood pressure management, anemia management, electrolyte management, uremia management, blood sugar level management, immune management or lipid management. Lifestyle habit improvement may be a recommendation to stop smoking or to reduce the BMI value to below 25. Dietary guidance may be salt or protein restriction. For blood pressure management, anemia management, electrolyte management, uremic toxin manage, blood sugar level management, immune management or lipid management in particular, treatment may involve administration of a drug. Blood pressure management may involve general management or administration of an antihypertensive drug, to reach below 130/80 mmHg. Antihypertensive drugs include diuretic drugs (thiazide diuretics such as trichlormethiazide, benzylhydrochlorothiazide and hydrochlorothiazide, thiazide-like diuretics such as meticrane, indapamide, tribamide and mefluside, loop diuretics such as furosemide, and potassium-sparing diuretics and aldosterone antagonists such as triamterene, spironolactone and eplerenone), calcium antagonists (dihydropyridine-based antagonists such as nifedipine, amlodipine, efonidipine, cilnidipine, nicardipine, nisoldipine, nitrendipine, nilvadipine, bamidipine, felodipine, benidipine, manidipine, azelnidipine and aranidipine, benzodiazepine-based antagonists, and diltiazem), angiotensin converting enzyme inhibitors (such as captopril, enalapril, acelapril, delapril, cilazapril, lisinopril, benazapril, imidapril, temocapril, quinapril, trandolapril and perindopril erbumine), angiotensin receptor antagonists (angiotensin II receptor antagonists such as losartan, candesartan, valsartan, telmisartan, olmesartan, irbesartan and azilsartan), and sympatholytic drugs (β-blockers, such as atenolol, bisoprolol, betaxolol, metoprolol, acebutolol, celiprolol, propranolol, nadolol, carteolol, pindolol, nipradilol, amosulalol, arotinolol, carvedilol, labetalol, bevantolol, urapidil, terazosin, prazosin, doxazosin and bunazosin). Erythropoietin formulations, iron agents and HIF-1 inhibitors are used as anemia treatments. Calcium receptor agonists (such as cinacalcet and etelcalcetide) and phosphorus adsorbents are used as electrolyte regulators. Active carbon is used as a uremic toxin adsorbent. Blood glucose level is managed to Hba1c of <6.9%, and in some cases a hypoglycemic agent is administered. Hypoglycemic agents that are used include SGLT2 inhibitors (such as ipragliflozin, dapagliflozin, luseogliflozin, tofogliflozin, canagliflozin and empagliflozin), DPP4 inhibitors (such as sitagliptin phosphate, vildagliptin, saxagliptin, alogliptin, linagliptin, teneligliptin, trelagliptin, anagliptin, omarigliptin), sulfonylurea agents (such as tolbutamide, acetohexamide, chlorpropamide, glyclopyramide, glibenclamide, gliclazide and glimepiride), thiazolidine agents (such as pioglitazone), biguanide agents (such as metformin and buformin), α-glucosidase inhibitors (such as acarbose, voglibose and miglitol), glinide agents (such as nateglinide, mitiglinide and repaglinide), insulin formulations and NRF2 activators (such as bardoxolonemethyl). Immunosuppressive agents (such as steroids, tacrolimus, anti-CD20 antibody, cyclohexamide and mycophenolate mofetil (MMF)) are used for immune management. Lipid management includes management to lower LDL-C to below 120 mg/dL, or in some cases dyslipidemia treatments are used, including statins (such as rosuvastatin, pitavastatin, atorvastatin, cerivastatin, fluvastatin, simvastatin, pravastatin, lovastatin and mevastatin), fibrates (such as clofibrate, bezafibrate, fenofibrate and clinofibrate), nicotinic acid derivatives (such as nicotinic acid derivatives (tocopherol nicotinate, nicomol and niceritrol), cholesterol transporter inhibitors (such as ezetimibe), PCSK9 inhibitors (such as evolocumab) and EPA formulations. All of these drugs may be used as single dosage forms for mixtures. Depending on the degree of renal function impairment, renal replacement therapy such as peritoneal dialysis, hemodialysis, continuous hemodialysis filtration, blood apheresis (such as blood plasma exchange or blood plasma adsorption) or kidney transplant may also be carried out.

Figure 5:
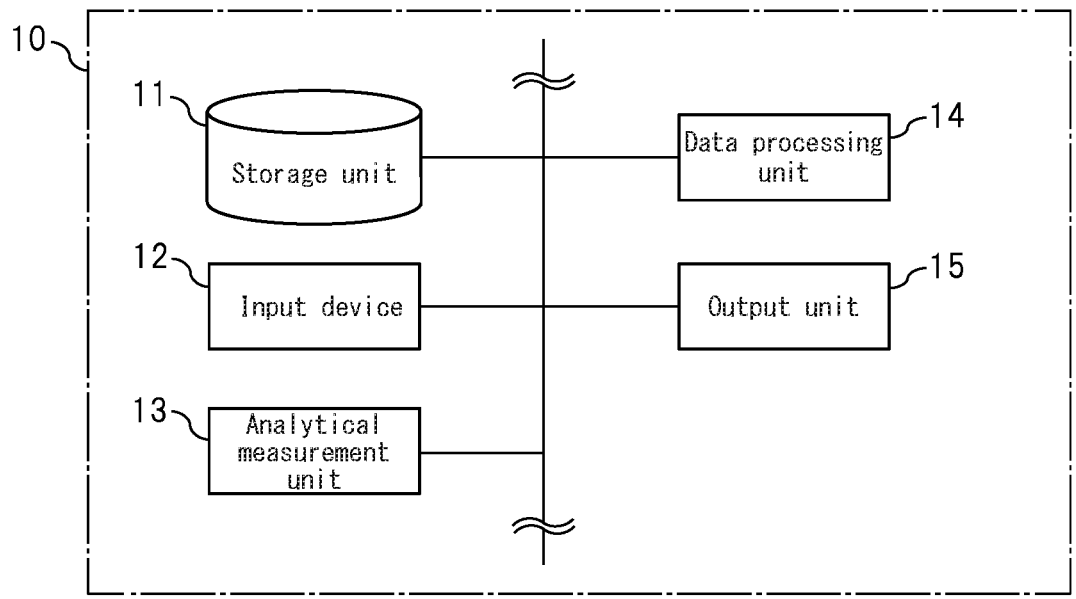
FIG. 5 is a block diagram of a sample analysis system of the invention.

Another aspect of the invention may relate to a sample analysis system and program for carrying out the method of determining glomerular filtration capacity. FIG. 5 is a block diagram of a sample analysis system of the invention. The sample analysis system 10 shown in FIG. 5 is constructed so as to allow the method of determining glomerular filtration capacity according to the invention to be carried out. The sample analysis system 10 comprises a storage unit 11, an input device 12, an analytical measurement unit 13, a data processing unit 14 and an output unit 15, and allows analysis of blood samples and output of glomerular filtration capacity.

More specifically, in the sample analysis system 10 of the invention:
the storage unit 11 stores a formula derived from the correlation between inulin clearance and D-serine levels in blood samples, inputted from an input device 12, or a corresponding table or graph,
the analytical measurement unit 13 separates and quantifies D-serine in a blood sample,
the data processing unit 14 either substitutes the D-serine level into the formula derived from the correlation between inulin clearance and D-serine level in blood samples, or reads from the corresponding table or graph, to determine the glomerular filtration capacity, and
the output unit 15 outputs the glomerular filtration capacity.

According to a more preferred mode, the sample analysis system of the invention may further include a step in which the storage unit 11 stores a threshold value inputted from the input device 12, and a step in which the data processing unit 14 compares the separated and quantified D-serine level with the threshold value. When the D-serine level is lower than the threshold value, the output unit 15 outputs an indication that the glomerular filtration capacity is high. When the D-serine level is higher than the threshold value, the data processing unit 14 either substitutes the D-serine level into the formula derived from the correlation between inulin clearance and blood sample D-serine levels, or reads it out from a corresponding table or graph, to determine the glomerular filtration capacity, and the output unit 15 outputs the glomerular filtration capacity.

The storage unit 11 has a portable storage device which may be a memory device such as a RAM, ROM or flash memory, a fixed disk device such as a hard disk drive, or a flexible disk or optical disk. The storage unit stores data measured by the analytical measurement unit, data and instructions inputted by the input device, and results of computation processing by the data processing unit, as well as the computer program and database to be used for processing by the information processing equipment. The computer program may be a computer readable recording medium such as a CD-ROM or DVD-ROM, or it may be installed via the internet. The computer program is installed in the storage unit using a commonly known setup program or the like. The storage unit stores data for the formula derived from the correlation between inulin clearance and blood sample D-serine levels, or for the corresponding table or graph, which have been inputted through the input device 12 beforehand. It may also store renal function categories corresponding to glomerular filtration rates.

The input device 12 is an interface and also includes operating units such as a keyboard and mouse. This allows the input device to input data measured by the analytical measurement unit 13 and instructions for computation processing to be carried out by the data processing unit 14. When the analytical measurement unit 13 is external, for example, the input device 12 may also include an interface unit allowing input of measured data through a network or storage medium, separately from the operating unit.

The analytical measurement unit 13 carries out the measuring step for D-serine in blood samples. The analytical measurement unit 13 therefore has a construction allowing separation and measurement of the D-forms and L-forms of amino acids. The amino acids may be analyzed one at a time, or some or all of the amino acid types may be analyzed at once. With no intention to be limitative, the analytical measurement unit 13 may be a chiral chromatography system comprising a sample introduction inlet, an optical resolution column and a detector, for example, and it is preferably a high-performance liquid chromatography system. From the viewpoint of detecting the levels of only specific amino acids, quantitation may be carried out by an enzyme method or immunological method. The analytical measurement unit 13 may be constructed separately from the sample analysis system, and measured data may be inputted through the input device 12 using a network or storage medium.

The data processing unit 14 can determine the glomerular filtration capacity by substituting from a measured D-serine level into the formula derived from the correlation between inulin clearance and blood sample D-serine levels, or reading it out from a corresponding table or graph. When the formula derived from the correlation between inulin clearance and blood sample D-serine level, or the corresponding table or graph, requires other correction values such as age, body weight, gender or body height, that information may also be inputted beforehand through the input device and stored in the storage unit. During calculation of the glomerular filtration rate, the data processing unit may access the information and input it into the formula, or read out a value from the corresponding table or graph, to calculate the glomerular filtration rate. The data processing unit 14 may also determine a kidney disease or renal function category from the determined glomerular filtration capacity. The data processing unit 14 carries out various computation processing operations on the data measured by the analytical measurement unit 13 and stored in the storage unit 11, based on a program stored in the storage unit. The computation processing is carried out by a CPU in the data processing unit. The CPU includes a functional module that controls the analytical measurement unit 13, input device 12, storage unit 11 and output unit 15, the functional module performing various control operations. Each of the units may be constructed by independent integrated circuits, microprocessors and firmware.

The output unit 15 is constructed so as to output the glomerular filtration capacity which is the result of the computation processing by the data processing unit. The output unit 15 may be output means such as a display device with a liquid crystal display that directly displays the computation processing results, or a printer, or it may be an interface unit for output to an external memory unit or output to a network. It may output the D-serine level and/or renal function category either together with the glomerular filtration capacity or independently.

Figure 6:
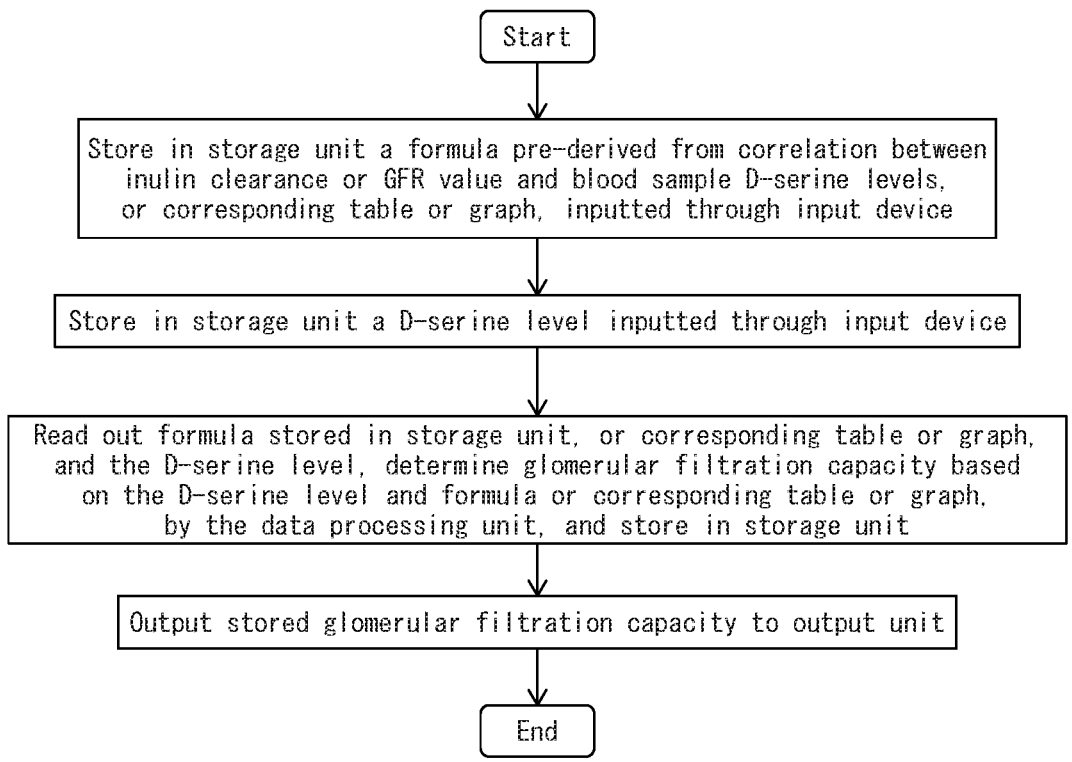
FIG. 6 is a flow chart showing an example of operation for determining glomerular filtration rate by the program of the invention.

FIG. 6 is a flow chart showing an example of operation for determining glomerular filtration rate by the program of the invention. Specifically, the program of the invention is a program that determines glomerular filtration rate in an information processing device comprising an input device, output unit, data processing unit and storage unit. The program of the invention includes a command for causing the information processing device:

to store a D-serine level inputted from an input device into a storage unit, to read out a formula derived from the correlation between inulin clearance and blood sample D-serine level or a corresponding table or graph, pre-stored in the storage unit, and a D-serine level, and to determine the glomerular filtration capacity in the data processing unit, to store the determined glomerular filtration capacity in the storage unit, and to output the stored glomerular filtration capacity to the output unit. The program of the invention may be stored in a storage medium, or it may be provided via electronic transmission such as the internet or a LAN.

When the information processing device comprises an analytical measurement unit, it may include a command for causing the information processing device to take the value for the blood sample measured by the analytical measurement unit and store it in the storage unit, instead of having the D-serine level value inputted from an input device.

All of the publications mentioned throughout the present specification are incorporated herein in their entirety by reference.

The examples of the invention described below are intended to serve merely as illustration and do not limit the technical scope of the invention. The technical scope of the invention is limited solely by the description in the Claims. Modifications of the invention, such as additions, deletions or substitutions to the constituent features of the invention, are possible so long as the gist of the invention is maintained.

EXAMPLES

Pool of Subjects

Eleven patients were used in a retrospective study, from among a cohort of chronic kidney disease (CKD) patients admitted to Osaka University Hospital, Department of Nephrology for diagnosis and/or treatment between 2016 and 2017. Separately, 15 healthy volunteers of age 20 and older were recruited by the National Institutes of Biomedical Innovation, Health and Nutrition. The test protocol was approved by the ethics committee of each facility, and written informed consent was obtained from all of the subjects.

The information for the healthy persons and chronic kidney disease patients were as follows:

TABLE 1

Baseline features for test subjects

| | Healthy test subjects n = 15 | CKD patients (n = 11) | P value |
|---|---|---|---|
| Age | 44 (39-50) | 50 (40-65) | 0.232 |
| Male percentage (%) | 80 (12) | 45.5 (5) | 0.103 |
| Body height (m) | 1.70 (1.68-1.75) | 1.63 (1.59-1.66) | 0.043 |
| Body weight (kg) | 68.9 (61.0-73.5) | 59.8 (51.5-66.7) | 0.194 |
| BSA ($m^2$) | 1.80 (1.72-1.90) | 1.61 (1.54-1.75) | 0.102 |
| BMI ($kg/m^2$) | 22.6 (21.1-25.7) | 22.5 (19.3-24.2) | 0.452 |
| Serum creatinine (mg/dL) | 0.75 (0.68-0.83) | 1.14 (0.75-2.59) | 0.069 |
| Serum cystatin C (mg/L) | 0.78 (0.69-0.84) | 1.14 (0.87-2.11) | 0.005 |
| Inulin clearance (mL/min/1.73 $m^2$) | 97.0 (94.1-107.3) | 46.0 (19.8-66.9) | <0.001 |

Values are represented as median (IQR) or % (count)

Inulin Clearance Measurement Method

Patient inulin clearance (Cin) was calculated from the blood and urine inulin concentrations, and urine volume, according to the standard method described in Clin Exp Nephrol 13, 50-54 (2009). In brief, 1% inulin (INULEAD injection, Fuji Yakuhin Co., Ltd.) was given by continuous intravenous drip infusion over a period of 2 hours while in a state of fasting, medication postponement and water load, and blood and urine samples were taken at 3 different time points during the period. The test subjects ingested 500 mL of water orally at 30 minutes before drip infusion. In order to maintain water load, 60 mL of water was ingested 40, 60 and 90 minutes after starting inulin drip infusion. The initial rate of drip infusion was 300 mL/h for the first 30 minutes, and 100 mL/h for the following 90 minutes. Blood samples were taken at 45, 75 and 105 minutes after the start of inulin drip infusion. The test subjects urinated to completely empty bladder at 30 minutes after the start of drip infusion. Urine samples were then taken during the period of 30 minutes to 60 minutes, 60 minutes to 90 minutes and 90 to 120 minutes thereafter. Inulin was measured using an enzyme method. The average of three Cin values was used as Cin (Cin-ST) according to a standard method.

Measurement of Blood D-Amino Acids

Sample Preparation

Sample preparation from human blood plasma was carried out in the following manner:

A 20-fold volume of methanol was added to the blood plasma and completely mixed with it. After centrifugation, 10 μL of supernatant obtained from the methanol homogenate was transferred to a brown tube and dried under reduced pressure. To the residue there were added μL of 200 mM sodium borate buffer (pH 8.0) and 5 μL of fluorescent labeling reagent (40 mM 4-fluoro-7-nitro-2,1,3-benzooxadiazole (NBD-F) in anhydrous MeCN), and the mixture was then heated at 60° C. for 2 minutes. The reaction was suspended by addition of 75 μL of aqueous 0.1% TFA (v/v), and 2 μL of the reaction mixture was supplied to two-dimensional HPLC.

Quantitation of Amino Acid Enantiomers by Two-Dimensional HPLC

The amino acid enantiomers were quantified using the following two-dimensional HPLC system. NBD derivatives of the amino acids were separated and eluted using a reversed-phase column (KSAA RP, 1.0 mm i.d.×400 mm; Shiseido Corp.), in the mobile phase (5 to 35% MeCN, 0 to 20% THF, 0.05% TFA). The column temperature was 45° C. and the mobile phase flow rate was 25 μL/min. The separated amino acid fraction was separated off using a multi loop valve, and optically resolved in a continuous manner with a chiral column (KSAACSP-001S, 1.5 mm i.d.×250 mm; Shiseido Corp.). The mobile phase used was a MeOH/MeCN mixed solution containing citric acid (0 to 10 mM or formic acid (0 to 4%), according to the amino acid retention. NBD-amino acids were detected by fluorescence detection at 530 nm using excitation light of 470 nm. The NBD-amino acid retention time was identified from standard amino acid enantiomers and quantified by a calibration curve.

Analysis of Correlation with GFR (Inulin Clearance)

(1) With Correction for Body Surface Area

The GFR (inulin clearance) corrected for body surface area, and the blood D-serine level (A), creatinine level (B) and cystatin C level (C), were plotted on a scatter plot for the 26 test subjects, and the correlation coefficient r and the p value were calculated. The results are shown in FIG. 1. The blood D-serine level was correlated with GFR (inulin clearance) in a manner equivalent with blood cystatin C level.

(2) Without Correction for Body Surface Area

Figure 2:
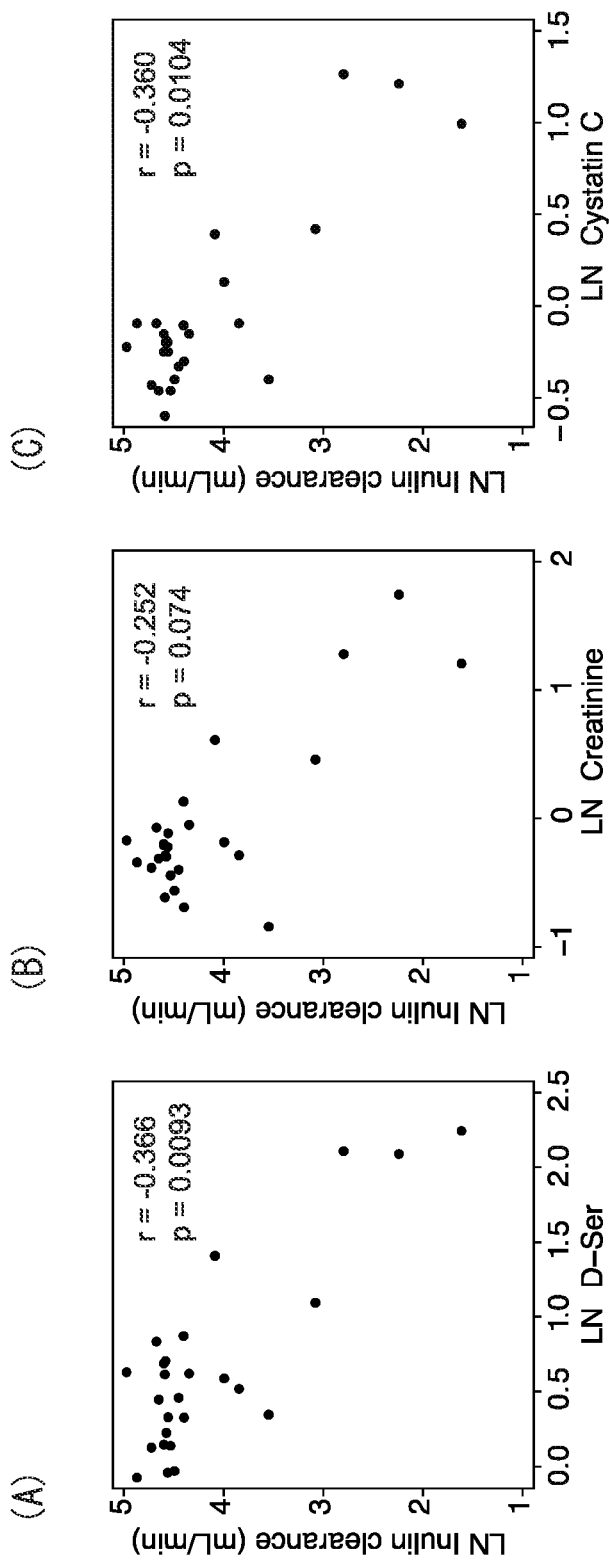
FIG. 2 is a set of scatter plots representing blood D-serine level (A), creatinine level (B) and cystatin C level (C) measured for subjects, with respect to GFR (inulin clearance) (not corrected for body surface area).

The GFR (inulin clearance), not corrected for body surface area, and the blood D-serine level (A), creatinine level (B) and cystatin C level (C), were plotted on a scatter plot for the 26 test subjects, and the correlation coefficient r and the p value were calculated. The results are shown in FIG. 2. The blood D-serine level showed highest correlation with GFR (inulin clearance) without correction for body surface area.

Correlation with Body Surface Area (BSA)

Figure 3:
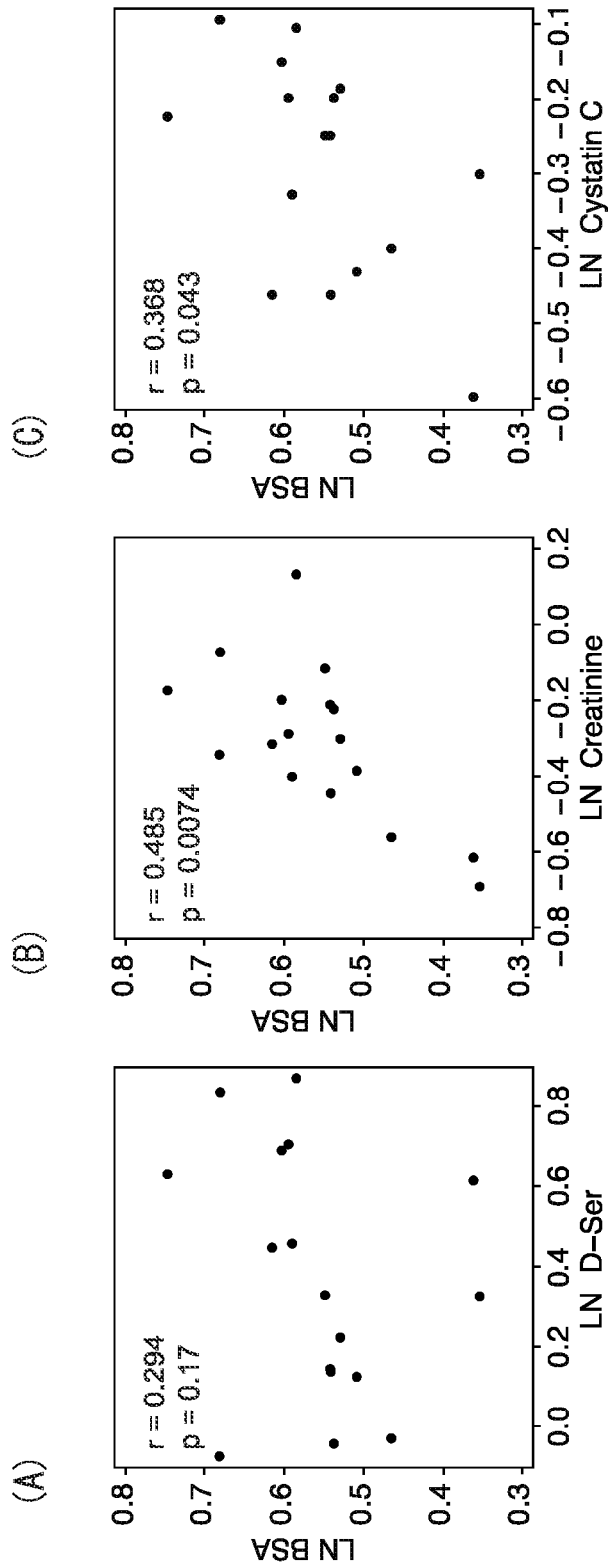
FIG. 3 is a set of scatter plots representing blood D-serine level (A), creatinine level (B) and cystatin C level (C) with respect to body surface area (BSA), from data for a healthy group (GFR>70).

Using the data for healthy subjects (GFR>70), the body surface area (BSA) and the measured blood D-serine level, cystatin C level and creatinine level were represented on a scatter plot and the correlation coefficient r and the p value were calculated. The results are shown in FIG. 3. The blood creatinine level and cystatin C level correlated with body surface area while the blood D-serine level did not correlate with body surface area.

Comparison Based on GFR Category

Figure 4:
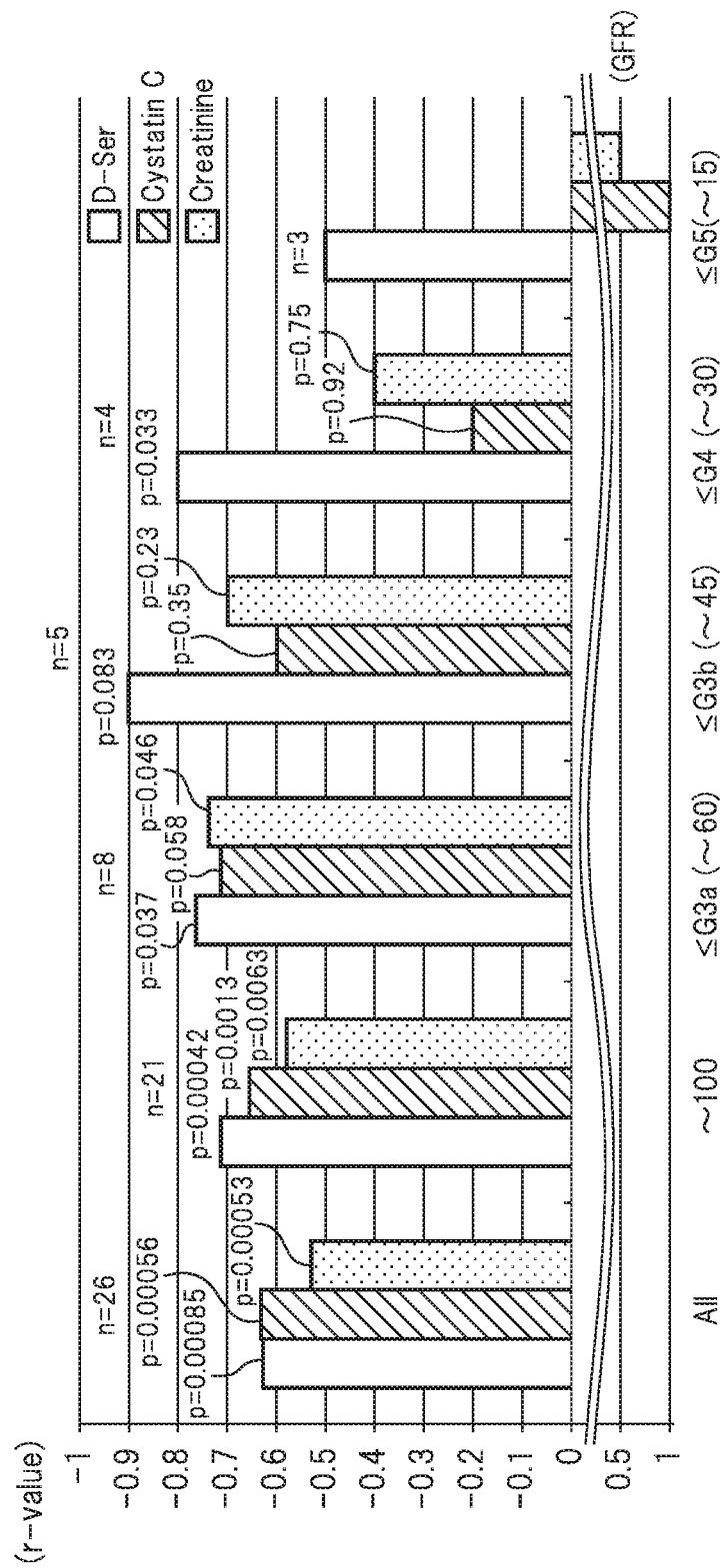
FIG. 4 is a graph showing the correlation between blood D-serine level (A), creatinine level (B) and cystatin C level (C) with GFR (inulin clearance) (corrected for body surface area), for each of the following categories: total data (All), GFR (inulin clearance) of ≤100, ≤G3a (GFR (inulin clearance) of ≤60); ≤G3b (GFR (inulin clearance) of ≤45); ≤G4 (GFR (inulin clearance) of ≤30); ≤G5 (GFR (inulin clearance) of ≤15).

The 26 test subjects were classified into the following groups based on GFR determined by inulin clearance: (total data (All); GFR of ≤100; ≤G3a: GFR of ≤60); ≤G3b (GFR of ≤45); ≤G4 (GFR of ≤30); ≤G5 (GFR of ≤15). There were 21 persons with GFR of ≤100, 8 with ≤G3a, 5 with ≤G3b, 4 with ≤G4 and 3 with ≤G5. For each set of data, the correlation coefficient r for the GFR (inulin clearance), not corrected for body surface area, and the blood D-serine level (A), creatinine level (B) and cystatin C level (C), as well as the p value, were calculated. The results are shown in FIG. 4. When grouped, the D-serine level showed the highest correlation with GFR (inulin clearance) in each group. Blood creatinine level in particular exhibited relatively satisfactory correlation with ≤G3a and ≤G3b, but the correlation was low with total data (All) and GFR of ≤100, a result that indicates the drawback of creatinine that it is not reflected in cases with mild renal function impairment. Cystatin C level, on the other hand, showed a high correlation with GFR (inulin clearance) in the data for relatively excellent renal function such as GFR≤100 and ≤G3a, although a lower correlation with GFR (inulin clearance) was shown as renal function declined, such as with ≤G3b. Blood D-serine level showed a satisfactory correlation with GFR (inulin clearance) in each group.

The invention claimed is:

1. A method of determining glomerular filtration capacity in a subject and treating a subject in need thereof, comprising:
   measuring D-serine levels from the blood of the subject;
   measuring inulin clearance of the subject;
   determining glomerular filtration capacity by determining glomerular filtration rate in the subject based on the correlation between the inulin clearance and the blood D-serine level; and
   carrying out treatment intervention when the subject is determined to have reduced glomerular filtration capacity,
   wherein the glomerular filtration rate is calculated using a formula selected from the Cockcroft-Gault formula, MDRD formula, and CKD-EPI formula; and
   wherein the treatment intervention includes:
   administration to the subject one or more drugs selected from the group consisting of diuretic drugs, calcium antagonists, angiotensin converting enzyme inhibitors, angiotensin receptor antagonists, sympatholytic drugs, SGLT2 inhibitors, sulfonylurea drugs, thiazolidine drugs, biguanide drugs, α-glucosidase inhibitors, glinide drugs, insulin formulations, NRF2 activators, immunosuppressive agents, statins, fibrates, anemia treatments, erythropoietin formulations, HIF-1 inhibitors, iron agents, electrolyte regulators, calcium receptor agonists, phosphorus adsorbents, uremic toxin adsorbents, DPP4 inhibitors, EPA formulations, nicotinic acid derivatives, cholesterol transporter inhibitors and PCSK9 inhibitors.

2. The method according to claim 1, where the blood is blood from a subject suspected of having kidney disease.

\* \* \* \* \*